United States Patent
Mizoguchi et al.

(10) Patent No.: US 9,642,988 B2
(45) Date of Patent: May 9, 2017

(54) CATHETER FIXATION DEVICE

(75) Inventors: Masato Mizoguchi, Shizuoka-ken (JP);
Masashige Hori, Shizuoka-ken (JP);
Masanori Makino, Shizuoka-ken (JP)

(73) Assignee: Covidien LP, Mansfield, MA (US)

( * ) Notice: Subject to any disclaimer, the term of this patent is extended or adjusted under 35 U.S.C. 154(b) by 831 days.

(21) Appl. No.: 13/595,052

(22) Filed: Aug. 27, 2012

(65) Prior Publication Data

US 2013/0079721 A1 Mar. 28, 2013

(30) Foreign Application Priority Data

Sep. 28, 2011 (JP) ................ 2011-213480

(51) Int. Cl.
*A61M 5/32* (2006.01)
*A61M 25/02* (2006.01)

(52) U.S. Cl.
CPC ....... *A61M 25/02* (2013.01); *A61M 2025/024* (2013.01); *A61M 2025/028* (2013.01)

(58) Field of Classification Search
CPC .................. A61M 25/02; A61M 2025/024
USPC .......... 604/174–175, 177–180; 206/363, 364
See application file for complete search history.

(56) References Cited

U.S. PATENT DOCUMENTS

| | | | |
|---|---|---|---|
| 4,170,995 A | 10/1979 | Levine et al. | |
| 4,224,937 A | 9/1980 | Gordon | |
| 4,250,880 A | 2/1981 | Gordon | |
| 4,397,647 A | 8/1983 | Gordon | |
| 4,449,975 A | 5/1984 | Perry | |
| 4,460,356 A | 7/1984 | Moseley | |
| 4,490,141 A | 12/1984 | Lacko et al. | |
| 4,527,559 A | 7/1985 | Roxburg et al. | |
| 4,563,177 A | 1/1986 | Kamen | |
| 4,678,462 A | 7/1987 | Vaillancourt | |
| 4,698,057 A | 10/1987 | Joishy | |
| 4,737,143 A | 4/1988 | Russell | |
| 4,808,162 A | 2/1989 | Oliver | |

(Continued)

FOREIGN PATENT DOCUMENTS

CN 201008697 1/2008
EP 1 048 320 11/2000
(Continued)

OTHER PUBLICATIONS

Australian Examination Report dated Apr. 30, 2013 in copending Australian Patent Appln. No. 2012216809.

(Continued)

*Primary Examiner* — Edelmira Bosques
(74) *Attorney, Agent, or Firm* — Kenneth Collier; Jessica Kwak Rauckman

(57) ABSTRACT

The present disclosure pertains to a fixing tool for holding a tubular catheter fixed in relation to the skin of a patient. This catheter fixing tool is equipped with a plate-shaped fixing tool main body and a securing member. The fixing tool main body has a retaining part, defining a catheter retaining slot, and a pair of wing pieces. The securing member can be interlocked with the fixing tool main body by rotating the securing member in a direction parallel to a principal surface of the fixing tool main body taking a virtual line perpendicular to the principal surface as the central axis C1. When securing member is rotationally interlocked with the fixing tool main body, the securing member presses the retaining part and the catheter securing slot is constricted. As a result, the catheter is held fixed by the securing member.

4 Claims, 6 Drawing Sheets

(56) References Cited

U.S. PATENT DOCUMENTS

| | | |
|---|---|---|
| 4,820,274 A | 4/1989 | Choksi |
| 4,826,486 A | 5/1989 | Palsrok |
| 4,863,432 A | 9/1989 | Kvalo |
| 4,898,587 A | 2/1990 | Mera |
| 4,976,698 A | 12/1990 | Stokley |
| 4,981,475 A | 1/1991 | Haindl |
| 5,084,026 A | 1/1992 | Shapiro |
| 5,215,532 A | 6/1993 | Atkinson |
| 5,300,037 A | 4/1994 | Delk et al. |
| 5,306,256 A | 4/1994 | Jose |
| 5,314,411 A | 5/1994 | Bierman et al. |
| 5,344,415 A | 9/1994 | DeBusk |
| 5,354,282 A | 10/1994 | Bierman |
| 5,372,589 A | 12/1994 | Davis |
| 5,380,294 A | 1/1995 | Persson |
| 5,413,562 A | 5/1995 | Swauger |
| 5,685,859 A | 11/1997 | Kornerup |
| 5,693,032 A | 12/1997 | Bierman |
| 5,810,781 A | 9/1998 | Bierman |
| 5,833,667 A | 11/1998 | Bierman |
| 5,885,254 A | 3/1999 | Matyas |
| 5,897,519 A | 4/1999 | Shesol et al. |
| 5,947,931 A | 9/1999 | Bierman |
| 6,113,577 A | 9/2000 | Hakky et al. |
| 6,231,548 B1 | 5/2001 | Bassett |
| 6,273,873 B1 | 8/2001 | Fleischer |
| 6,290,676 B1 | 9/2001 | Bierman |
| 6,302,867 B1 | 10/2001 | Brown, Jr. et al. |
| 6,311,933 B1 | 11/2001 | Starchevich |
| 6,428,515 B1 | 8/2002 | Bierman et al. |
| 6,582,403 B1 | 6/2003 | Bierman et al. |
| 6,673,046 B2 | 1/2004 | Bierman et al. |
| 7,014,627 B2 | 3/2006 | Bierman |
| 7,018,362 B2 | 3/2006 | Bierman et al. |
| 7,119,247 B2 | 10/2006 | Worthley |
| 7,153,291 B2 | 12/2006 | Bierman |
| 7,220,246 B2 | 5/2007 | Raulerson et al. |
| D547,862 S | 7/2007 | Dikeman et al. |
| 7,413,561 B2 | 8/2008 | Raulerson et al. |
| 2002/0188255 A1 | 12/2002 | Bierman et al. |
| 2005/0027258 A1 | 2/2005 | Bierman et al. |
| 2006/0058738 A1 | 3/2006 | Ponzi |
| 2006/0129103 A1 | 6/2006 | Bierman et al. |
| 2006/0161109 A1 | 7/2006 | Huet |
| 2006/0264836 A1 | 11/2006 | Bierman |
| 2008/0065022 A1 | 3/2008 | Kyvik et al. |
| 2008/0097334 A1 | 4/2008 | Dikeman et al. |
| 2008/0171993 A1 | 7/2008 | Beran |
| 2008/0200880 A1 | 8/2008 | Kyvik et al. |
| 2008/0249476 A1 | 10/2008 | Bierman |
| 2009/0093769 A1 | 4/2009 | Wright et al. |

FOREIGN PATENT DOCUMENTS

| | | |
|---|---|---|
| GB | 2 333 234 | 7/1999 |
| JP | 2003 062083 | 3/2003 |
| WO | WO 98/15312 | 11/2000 |
| WO | WO 02/11786 A2 | 2/2002 |
| WO | WO 2004/026161 | 4/2004 |
| WO | WO 2008/054761 | 5/2008 |
| WO | WO 2010/002393 | 1/2010 |

OTHER PUBLICATIONS

U.S. Appl. No. 13/595,094, filed Aug. 27, 2012, Masanori Makino.
European Search Report dated Nov. 6, 2012 in copending European Appln. No. 12183339.
European Search Report dated Nov. 6, 2012 in copending European Appln. No. 12183340.
European Search Report dated Feb. 21, 2012 in corresponding European Appln. No. 09818393.
Written Opinion and International Search Report in International Application No. PCT/US2009/058909 filed Sep. 30, 2009.
Chinese Office Action dated Oct. 26, 2012 in copending Chinese Application No. 200980138766.

(a)

(b)

CATHETER FIXATION DEVICE

CROSS REFERENCE TO RELATED APPLICATION

This application claims the benefit of and priority to Japanese Patent Application Serial No. 2011-213480 filed Sep. 28, 2011, the entirety of which is incorporated herein by reference.

BACKGROUND

Technical Field

The present invention pertains to a catheter-fixing tool for fixing a catheter to a patient's skin.

Description of Related Art

In recent years, treatment and diagnosis in medical settings have been performed making widespread use of catheters. Because at the time of use it is necessary to reliably hold the catheter tip in place at an appropriate site for diagnosis or treatment, the external part of this type of catheter that comes out of the skin is generally fixed to the patient.

Catheter fixing tools used when a catheter is fixed to the surface of a patient's body have been proposed in the past as a means for securing the catheter to the patient. Catheter fixing tools of this type, for example, have been equipped with a fixing tool main body consisting of soft resin and securing member components composed of metal or resin which are stiffer than the fixing tool main body.

A retaining part able to insert and locate the catheter is provided in the fixing tool main body. In the state where the catheter is inserted and located, the catheter periphery is for the most part covered by the retaining part. In order to give a sufficient stiffening effect to the fixing tool main body, the securing member covers the fixing tool main body from above. As a result, by tightly fastening the retaining part, the catheter becomes securely held in place.

Several other proposals have been made as previously existing technology for this sort of catheter fixing tool. See for example, Unexamined Japanese Application Publication No. 2003-154012 and Unexamined Patent Application Publication No. 2008-212434. In addition to tools separately configured as fixing tool main body and securing member, there are also interlocking and integrated tools.

However, in conventional catheter fixing tools, because a pressing force is added onto the skin when the securing member covers and interlocks from the vertical direction of the fixing tool main body, the skin is compressed, and a physical burden is placed on the patient. In addition, because a patient's skin has elasticity, there is the drawback that it is difficult to insert the catheter into the retaining part.

At this point, when covering and interlocking the securing member to the fixing tool main body, if it is possible to access the securing member not from the top but from the side of the fixing tool main body, compression of the skin is thought to become less likely. In this case, it is necessary to initially locate the securing member having it protrude out to a large extent from the fixing tool main body and for sliding to start from this position, hence, is necessary to assure in advance that there is space on the periphery of the catheter-fixing tool. However, in addition to the fact that skin is uneven rather than flat, other medical devices or equipment and the like may also be placed around the catheter fixing tool.

Because of this, depending on circumstances it is not necessarily a simple matter to assure there is space for the sliding operation. Consequently, construction of a catheter fixing tool is desired that saves space and can be manipulated to put on and take off The present invention has taken into account the aforementioned problem. The object of the present invention is to provide a catheter fixing tool that can stably hold a catheter fixed without putting excessive burden on a patient when it is fixed on the patient and that can be operated in a space-saving manner

SUMMARY

Four embodiments for solving the problem are enumerated below. In a first embodiment, a catheter-fixing tool for securing a tubular catheter is equipped with a plate-shaped fixing tool main body having a retaining part, into which is formed a catheter retaining slot, and pair of wing parts, and a securing member that can be interlocked with the fixing tool main body by rotation parallel to the principal plane taking a virtual line perpendicular to the principal plane of the fixing tool as the central axis, wherein the retaining part is pressed by the securing member to constrict the catheter retaining slot when rotationally interlocked with the securing member.

Thus, according to the invention described in embodiment 1, the securing member interlocks with the fixing tool main body by rotation parallel to the principal plane taking a virtual line perpendicular to the principal plane of the fixing tool main body as the central axis. At this time, the retaining part of the fixing tool main body is depressed by the securing member, and the catheter-retaining slot is constricted. As a result, the catheter is secured and stably held fixed by the retaining part. In addition, because the securing member can be interlocked by rotating in a direction parallel to the direction of the principal plane, it is difficult for a compressive force in the vertical direction to be imparted on the skin. Therefore, the catheter can be held fixed without putting excessive burden on the patient. Furthermore, different from a system in which the securing member is interlocked by sliding it on, if the system is one in which the securing member is interlocked by rotating it, it becomes unnecessary to initially position the securing member having it protrude out to a large extent from the fixing tool main body. Thus, a large amount of space for manipulation around the catheter-fixing tool becomes unnecessary, and designing can be done to save space.

In a second embodiment, the catheter fixing tool described in embodiment 1 includes a securing member which is formed to be smaller than the fixing tool main body in a plan view, and the virtual line is set roughly in the center of the retaining part and roughly in the center of the securing member.

Thus, according to the invention described in embodiment 2, because of the fact that the location of the virtual line that forms the central axis when rotationally interlocked is set as described above relative to the sizes of the securing member and the fixing tool main body, the securing member can be made so that it does not protrude laterally from the fixing tool main body from the start to the conclusion of the rotational interlocking movement. Therefore, designing can certainly be done to save space.

In a third embodiment, the catheter fixing tool described in embodiments 1 or 2 includes a securing member defining a cover that completely covers the retaining part in a state where the back side of the securing member is brought into contact with the top of the retaining part.

Thus, according to the invention described in embodiment 3, because the back surface of the cover, which is the securing member, and the top of the retaining part are in a state of contact, the overall thickness of the catheter-fixing tool can certainly be held down. Furthermore, because of the fact that the retaining part overall is covered by a cover, the securing part and the catheter secured in that location will not directly contact the dressing. Because of this, shifting of the catheter with the removal of a dressing and other such problems can be avoided.

In a fourth embodiment, the catheter fixing tool described in embodiments 1 to 3 includes guide parts extending in the principal surface direction of the fixing tool main body in the outer peripheral surface of the securing part, and guided parts that can lock into the guide part in the external peripheral part of the back side of the securing member.

Thus, according to the invention described in embodiment 4, because the guided parts can lock into the guide parts, the securing member can smoothly rotate while being guided along the planar direction of the fixing tool main body. In addition, when the securing member is in the interlocked state with the fixing tool main body, it is difficult for the securing member to come out of the fixing tool main body.

Positioning parts may be provided respectively for the fixing tool main body and the securing member.

Thus, according to this construction, by the positional relationship of the positioning parts provided in the fixing tool main body and securing member, the positioned state of both can be understood.

As described in detail above, according to the invention described in embodiments 1 to 4, a catheter fixing tool can be provided that can stably hold a catheter without putting excessive burden on a patient when it is fixed on the patent and that can be operated in a space-saving manner

DETAILED DESCRIPTION OF EMBODIMENTS

Catheter fixing tool 11 of Embodiment 1 that embodies the present invention is described in detail based on FIG. 1 to FIG. 4.

Catheter fixing tool 11 of this embodiment is a medical device used when holding tubular catheter 1 fixed.

Figure 3:
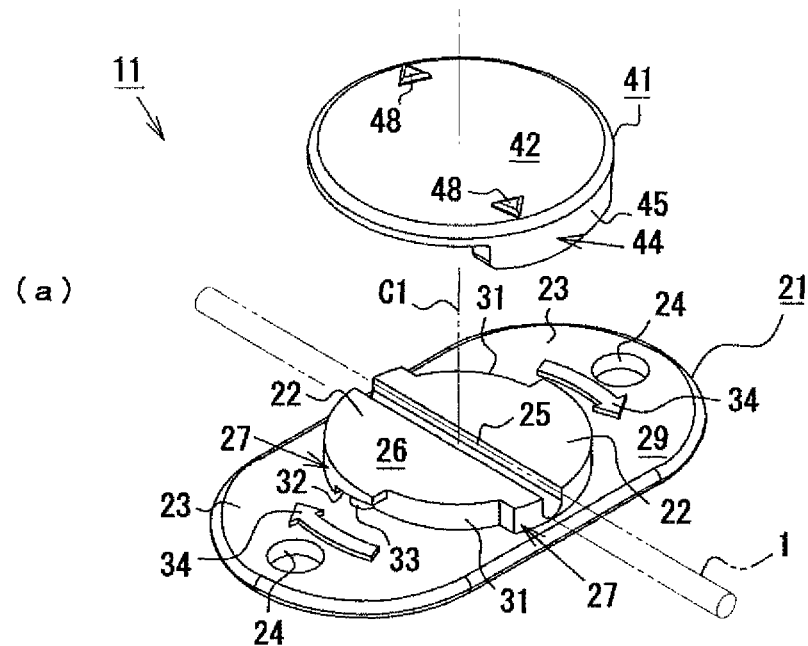
FIGS. 3(a) and (b) are perspective views illustrating the securing member and the holding tool main body of the aforementioned catheter fixing tool prior to and after connection.
Figure 3:
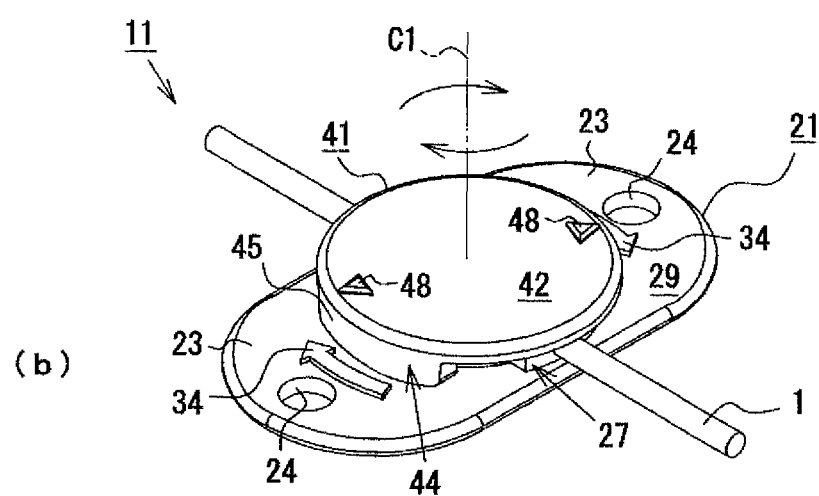
Figure 4:
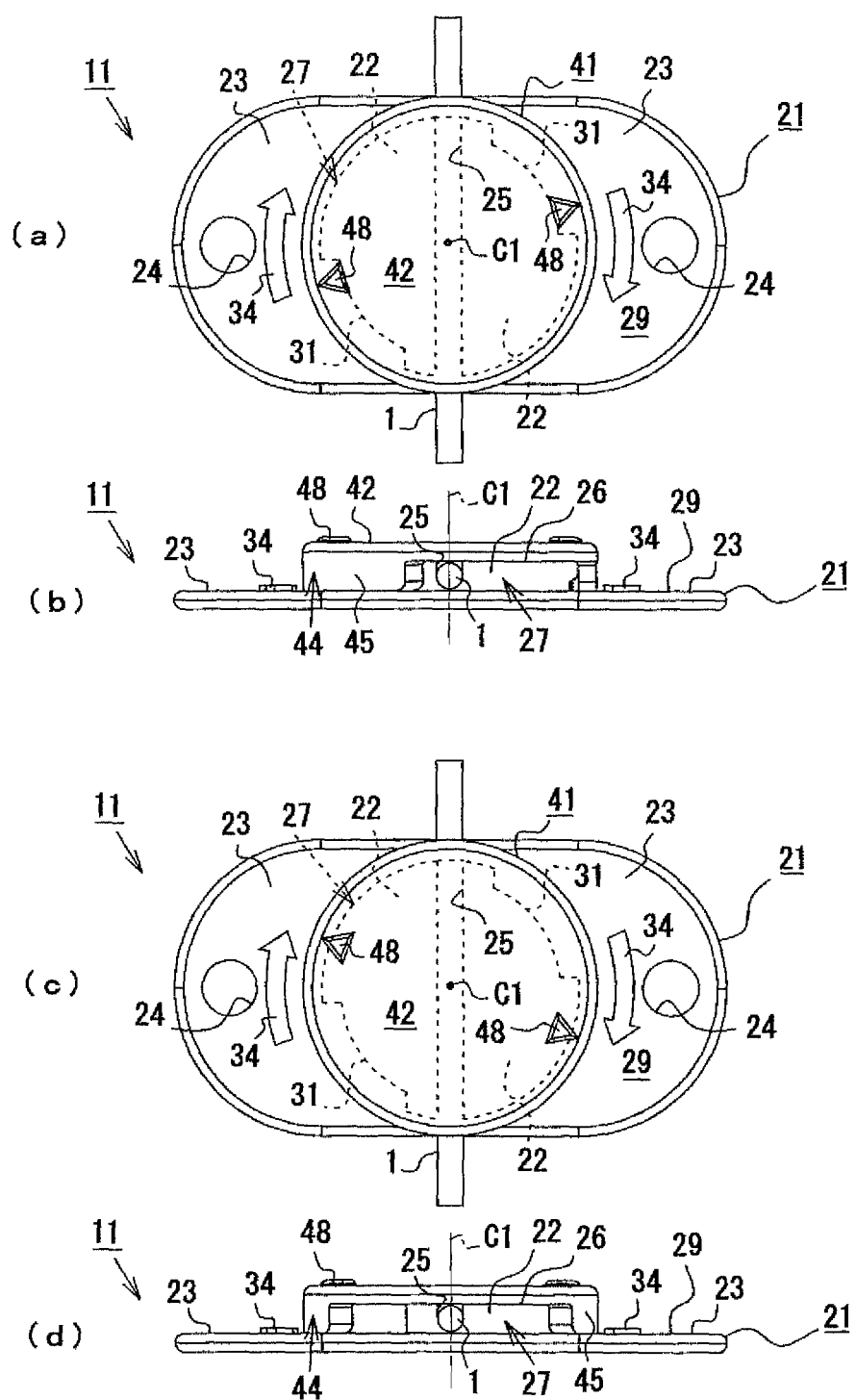
FIG. 4(a) is a plan view of the catheter fixing tool before rotating the securing member to rotationally interlock the pieces, (b) is front view of the same, (c) is a plan view of the catheter fixing tool after rotating the securing member to rotationally interlock the pieces, and (d) is a front view of the interlocked pieces shown in FIG. 4(c).

The catheter fixing tool 11 is made up of basically two components as shown in FIG. 3 and FIG. 4 (fixing tool main body 21 and cover 41 as a securing member).

Figure 1:
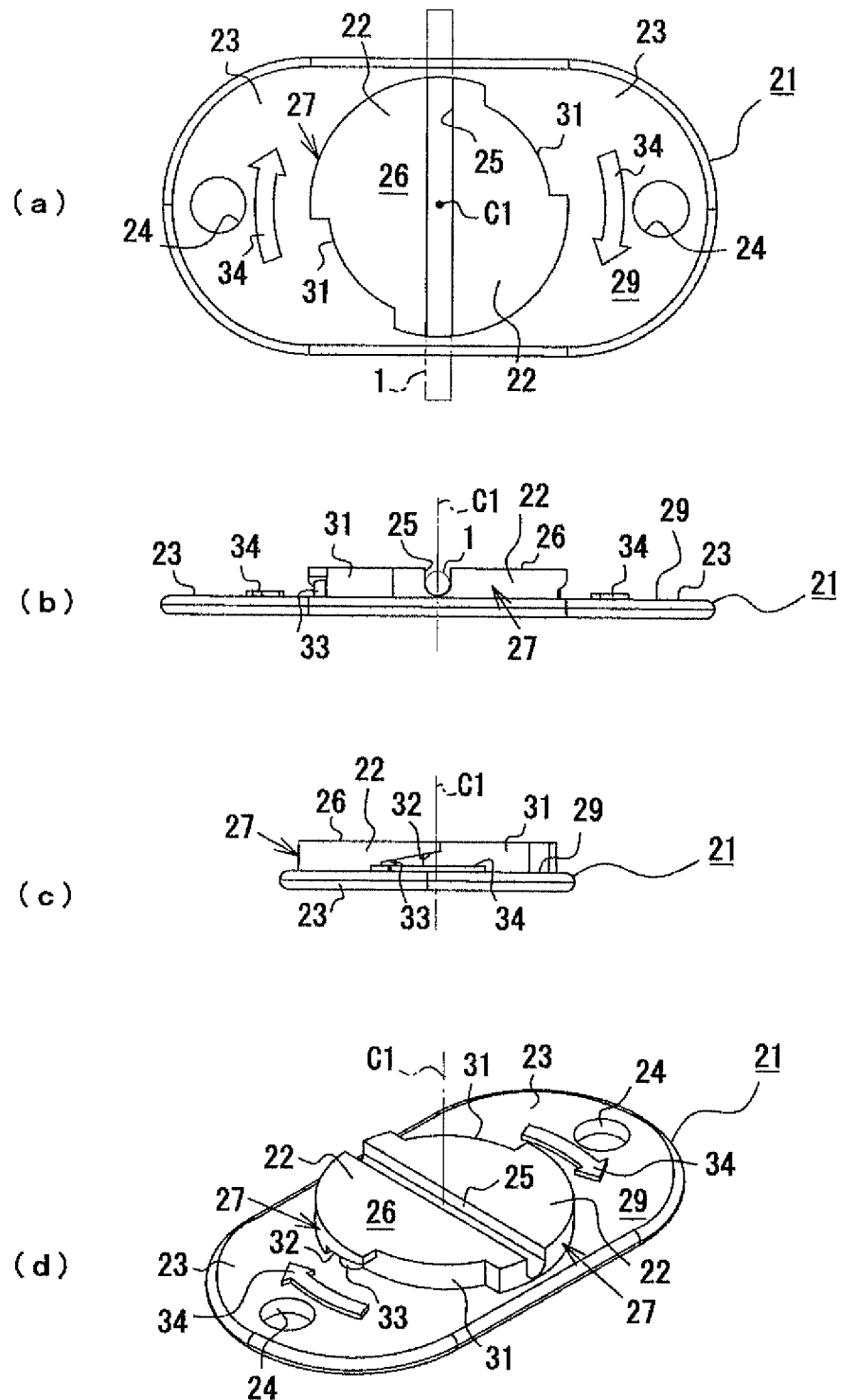
FIG. 1(a) is a plan view showing the fixing tool main body of the catheter fixing tool of one embodiment of the present invention, (b) is a front view of the fixing tool main body shown in FIG. 1(a), (c) is a side view of the fixing tool main body shown in FIGS. 1(a), and (d) is a perspective view of the fixing tool main body shown in FIG. 1(a).

As shown in FIG. 1 and FIG. 3, fixing tool main body 21 is a plate-shaped member that has an oblong shape in planar view and is formed using a comparatively soft synthetic resin material (for example, a polyamide-type elastomer). In addition to polyamide-type elastomers, soft synthetic resin materials can be selected such as, for example, polyvinyl chloride, silicone rubber, soft polyurethane, and polyamide-type elastomers. Here, because fixing tool main body 21 is a member that contacts skin directly, it is preferable to use material that has flexibility and elasticity to lessen the sense of discomfort imparted to the patient. In addition, the synthetic resin material from which fixing tool main body 21 is formed is preferably softer than the tubular body material of catheter 1. The reason for this is to avoid deforming catheter 1 and crushing the lumen when adding a pressing force by holding catheter 1 in fixing tool main body 21.

Fixing tool main body 21 has a pair of wing pieces 23. These wing pieces 23 are provided with circular holes 24. These holes 24 are through holes for inserting sutures. An adhesive layer in the back side of fixing tool main body 21 for adhesively fixing tool main body 21 to the skin may include a coating of adhesive or attached adhesive sheet. In addition, a release film for protecting this adhesive layer in its pre-use condition may be applied. Retaining part 22 is provided and protrudes out from the central part of the principle surface 29 side of fixing tool main body 21. Catheter retaining slot 25 is built into this retaining part 22 so as to be able hold catheter 1. Catheter retaining slot 25 extends along a direction that crosses fixing tool main body 21 and opens onto the principal plane 29 side of fixing tool main body 21.

As shown in FIG. 1 and FIG. 3, etc., in the peripheral part of the circle, retaining part 22 has two cut-out shapes that are circular arc-shaped in plan view. The two circular arc-shaped cut out parts 31 in retaining part 22, which holds catheter retaining slot 25, and crosses the center of retaining part 22, are in an opposing positional relationship. Guide slots 32 are provided as a guide part that extends in the principal plane 29 direction of fixing tool main body 21 in the peripheral surface 27 of retaining part 22. Guide slots 32 open onto circular arch-shaped cutouts 31, and extend along the circumferential direction of retaining part 22 (that is, parallel to the direction of principal plane 29). As shown in FIGS. 1(c) and (d), a slanted wall defines slots 32 such that slots 32 become narrower as it goes back. In addition, the virtual line that passes through the center of retaining part 22 perpendicular to principal surface 29 of fixing tool main body 21 denotes the central axis C1 when rotating cover 41 as the securing member.

Figure 2:
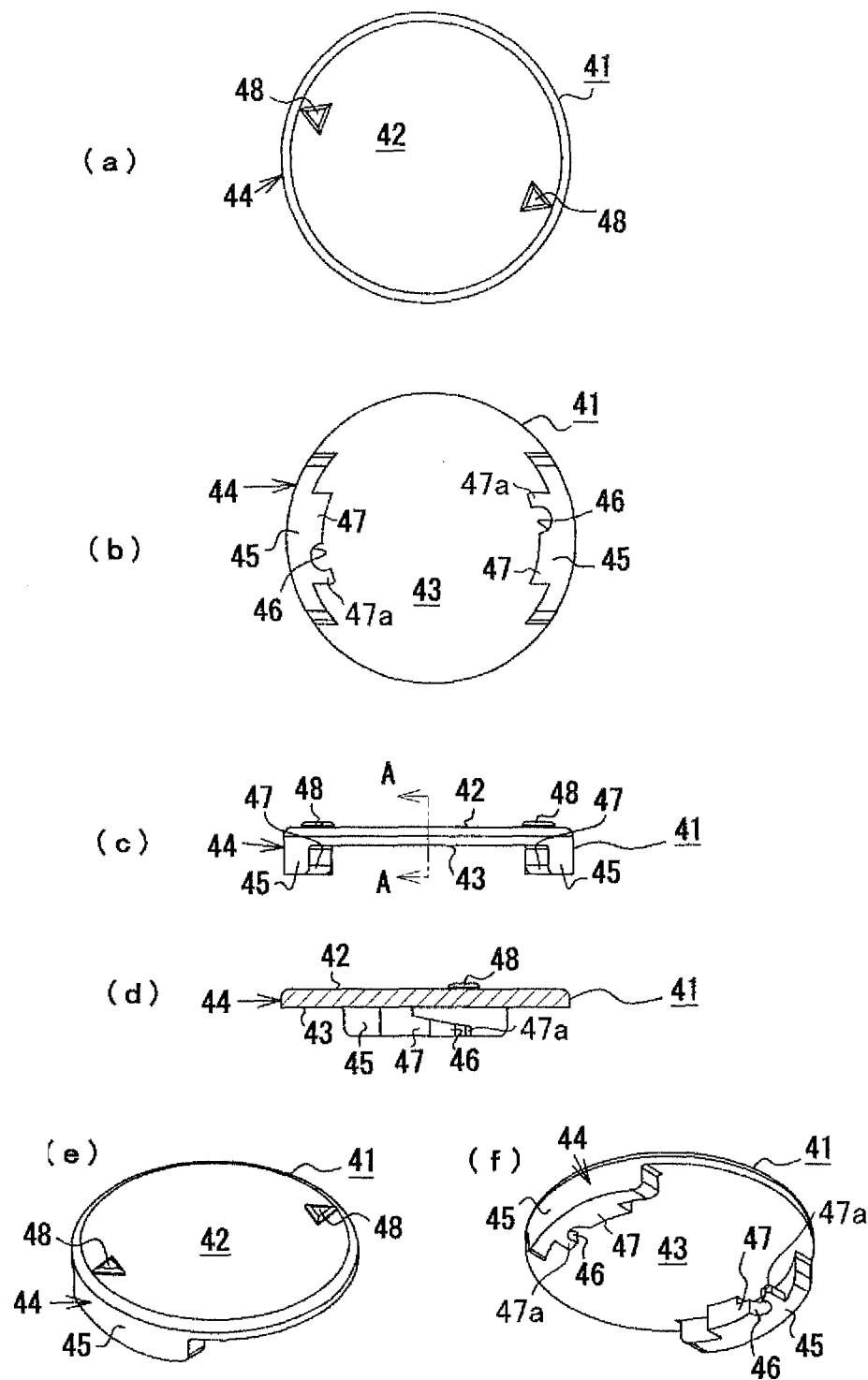
FIG. 2(a) is a plan view of the securing member of the presently disclosed catheter fixing tool, (b) is a bottom view of the securing member shown in FIG. 2(a), (c) is a front view of the securing member shown in FIG. 2(a), (d) is a view of cross section taken along section line A-A of FIG. 2(c), (e) is a perspective view viewed from above of the securing member shown in FIGS. 2(a), and (f) is a perspective view viewed from below of the securing member shown in FIG. 2(b).

Cover 41 as the securing member is shown in FIG. 2, FIG. 3, and elsewhere. The cover is made using synthetic resin material that is harder than the synthetic resin material that makes up fixing tool main body 21 (for example, polypropylene). In addition to polypropylene, hard synthetic resins may be selected such as polyethylene, polycarbonate, polyamide, polyester, polyoxymethylene, rigid polyurethane, and ABS. Cover 41 has a front surface 42 and a back surface 43, which is positioned to come in contact with top surface 26 of retaining part 22. This cover 41 has a size that can completely cover retaining part 22 in the state where back surface 43 is brought in contact with top surface 26 of retaining part 22. Note that cover 41 is somewhat larger than retaining part 22 and is a circular shaped member about half the size of fixing tool main body 21.

In the circumferential part 44 on the back surface 43 side of cover 41, a pair of guided parts 45 are provided positioned apart that project out along a circular arc. These guided parts 45 have salient guided parts 47, which protrude toward the center of cover 21 on the inner side. In addition, a semicircular-shaped locking recessed part 46 is built into the guided part 47 which is capable of engaging and disengaging with engagement protrusion 33 in the side of retaining part 22. Note that tip 47a of salient guided part 47 is the part with the furthest projection toward the center of cover 41.

In the space between retaining part 22 and hole 24 in the principal surface of fixing tool main body 21, a pair of positioning marks 34 are provided as positioning parts. These positioning marks 34 are slightly curved arrows and are located along the circular arc of retaining part 22. On the other hand, triangular-shaped positioning marks 48 (FIG. 2(e)) are provided as positioning parts in two locations on the circumferential part 44 of top surface 42 of cover 41. In this embodiment, when positioning marks 48 on the side of cover 41 reach the vicinity the proximal ends of arrow-shaped positioning marks 34 on the side of fixing tool main body 21, the positional relationship of both are set so that they are in a fully mated position. When in a fully mated condition, the inner surface tip 47a of salient guided part 47 is in an inserted and locked condition in guide slot 32. At this time, the inner surface of tip 47a of salient guided part 47 is in contact from two directions with sides in a region further back than engagement protrusion 33 of guide slot 32 so as to add a pressing force toward the center of retaining part 22 (that is, a direction that holds retaining slot 25). There are the following advantages to a construction such as this in which a pressing force is exerted not by the overall salient guided part 47 but only a part (in brief, pressing force on a comparatively small surface). That is, while reducing sliding friction to maintain ease of rotation when rotationally moving cover 41, sufficient pressing force can be added in a fully mated condition to one end and the other end of the longer direction of catheter retaining slot 25.

Next, the procedure for fixing catheter 1 by using catheter fixing tool 11 of this embodiment constructed as described above is described based on FIG. 3 and FIG. 4.

For example, consider the case where the tip of catheter 1 is guided percutaneously in the subclavian vein, and the remainder of catheter 1 is led outside the skin from the puncture point in the precordia of the patient. Then, catheter fixing tool 11 is attached to an external part of catheter 1 leading outside of the skin.

First, after inserting the external part of catheter 1 into catheter retaining slot 25, which is made up of fixing tool main body 21 and retaining part 22 (see FIG. 3(a)), position fixing tool main body 21 over the skin. When there is an adhesive layer on the bottom side of fixing tool main body 21, fixing tool main body 21 can be affixed to the skin by means of the adhesive layer at this stage.

Next, hold cover 41 between fingers to position it just above retaining part 22 of fixing tool main body 21, access fixing tool main body 21 from this position, and position cover 41 so as to cover retaining part 22 (see FIG. 3(a)). At this time, as shown in FIG. 4(a) and FIG. 4(b), arrange positioning marks 48 on the side of cover 41 so that they are located near the proximal end of arrow-shaped positioning marks 34 on the side of fixing tool main body 21. When in this positional state, position guided parts 45 precisely on circular-arch-shaped cut outs 32. Rotate cover 41 in a clockwise direction taking as the center the central axis C1, which was set as the center of retaining part 22 and the center of cover 41 in a planar view, and salient guided parts 43 will gradually move into guide slots 32. At this time, salient guided parts 47 are smoothly guided by guide slots 32.

As shown in FIG. 3(b), FIG. 4(c) and FIG. 4(d), rotationally move cover 41 until the positioning marks 48 on the sides of cover 41 come near the tips of the arrow-shaped positioning marks 34 of fixing tool main body 21. Thereupon, salient guided parts 47 fully move into guide slots 32, and cover 41 cannot be further rotated. In addition, locked recessed parts 46 (FIG. 2(b)) on the side of cover 41 reach the position of engagement protrusions 33 on the side of fixing tool main body 21, and they mutually engage. At this time, because the practitioner gets a click sensation at the fingertips, the practitioner can understand by tactile sensation that the pieces are in a fully interlocked condition. When fully interlocked in this manner, retaining part 22 is pressed upon from the left and right sides by tips 47A of salient guided parts 47, and by inducing a deformation in retaining part 22, catheter retaining slot 25 is constricted. As a result, the external part of catheter 1 is fastened tightly by retaining part 22 and fixed solidly in catheter retaining slot 25. In the completely interlocked state, the back surface 43 (FIG. 2(f)) of cover 41 and the top surface 26 of retaining part 22 are in a state of contact, and retaining part 22 is in a condition where it is almost entirely covered by cover 41. Subsequently, a dressing may be applied as necessary to protect the catheter fixing tool 11 and insertion site.

When it is desired to release hold of catheter fixing tool 11 to remove catheter 1, carry out the opposite actions as when rotationally interlocking the parts as described above. In cases where a dressing has been applied, first remove the dressing to expose catheter fixing tool 11. At this time, although it is easy for an upward force to be imparted on catheter fixing tool 11, it is difficult for a force to be exerted in a direction to remove cover 41, and hence, the risk of removing cover 41 with the dressing is extremely small. Furthermore, the fact that salient guided parts 47 of guided parts 45 are locked into guide slots 32 contributes to preventing displacement of cover 41. Next, rotate cover 41 in an anticlockwise direction, and disengage cover 41 from fixing tool main body 21. At this time, the catheter retaining slot that had been constricted by the pressing of retaining part 22 expands, and by releasing the hold on catheter 1, catheter 1 can be taken out.

Consequently, the following effects can be obtained according to this embodiment.

(1) According to the make up of catheter fixing tool 11 of this embodiment, cover 41 interlocks with fixing tool main body 21 by rotating in a direction parallel to principal surface 29 taking a virtual line perpendicular to principal surface 29 of fixing tool main body 21 as the central axis C1. At this time, cover 21 presses upon retaining part 22 of fixing tool main body 21, and catheter retaining slot 25 is constricted. As a result, catheter I is fastened tight and fixed securely by retaining part 22. In addition, because cover 41 can be interlocked by rotation in a direction parallel to principal surface 29, it becomes difficult to add a pressing force perpendicular to the skin. Therefore, catheter 1 can be held fixed without putting excessive burden on the patient. Furthermore, since it is difficult for a force to be imparted in a direction to remove cover 41 even when removing a dressing, it is difficult for sudden situations to occur such as those in which the cover is removed together with the dressing.

(2) In this embodiment, different from systems in which cover 41 is locked by sliding, because it is a system in which cover 41 is interlocked with fixing tool main body 21 by rotation, it is not necessary to initially position cover 41 having it laterally protrude out to a large extent from fixing tool main body 21. Moreover, in addition to the fact that cover 41 is a circular plate shaped member that is formed smaller than fixing tool main body 21 in a plan view, the central axis Cl in a plan view is set to the center of retaining part 22 and the center of cover 41. Consequently, cover 41 can be made so that it does not laterally protrude from fixing tool main body 21 from the start to finish of the rotational interlocking movement. Thus, a large amount of space for manipulation around the catheter fixing tool becomes unnecessary, and designing can certainly be done to save space.

(3) With the catheter fixing tool 11 of this embodiment, because the back surface 43 of cover 41, which is the securing member, and the top surface 21 of retaining part 22 are in a state of contact, the overall thickness of catheter fixing tool 11 can certainly be held down. Because of the fact that retaining part 22 is wholly covered by cover 41, retaining part 22 and catheter 1, which is held there, do not directly contact the dressing. Because of this, shifting of the catheter with the removal of the dressing and other such problems can be avoided.

(4) For the case of catheter fixing tool 11 of this embodiment, positioning marks 34 and 48 are provided in fixing tool main body 21 and cover 41, respectively. Consequently, according to this construction, the positional state of fixing tool main body 21 and cover 41 can be easily understood visually by the mutual positional relationship of positioning marks 34 and 48.

(5) In this embodiment, because cover 41 includes a synthetic resin material that is harder than fixing tool main body 21, retaining part 22, which includes a relatively soft resin material, is efficiently pressed upon. Consequently, retaining slot 25 is positively constricted by positive deformation of retaining part 22. For this reason, catheter 1 is more strongly held tight and fixed by retaining part 22. In addition, because of the fact that fixing tool main body 21 and cover 41 are both made of synthetic resin material, there is the advantage with this embodiment that it is not particularly necessary to remove it even at the time of an examination using magnetic resonance imaging (MRI).

The embodiment of the present invention may be changed as follows.

Figure 5:
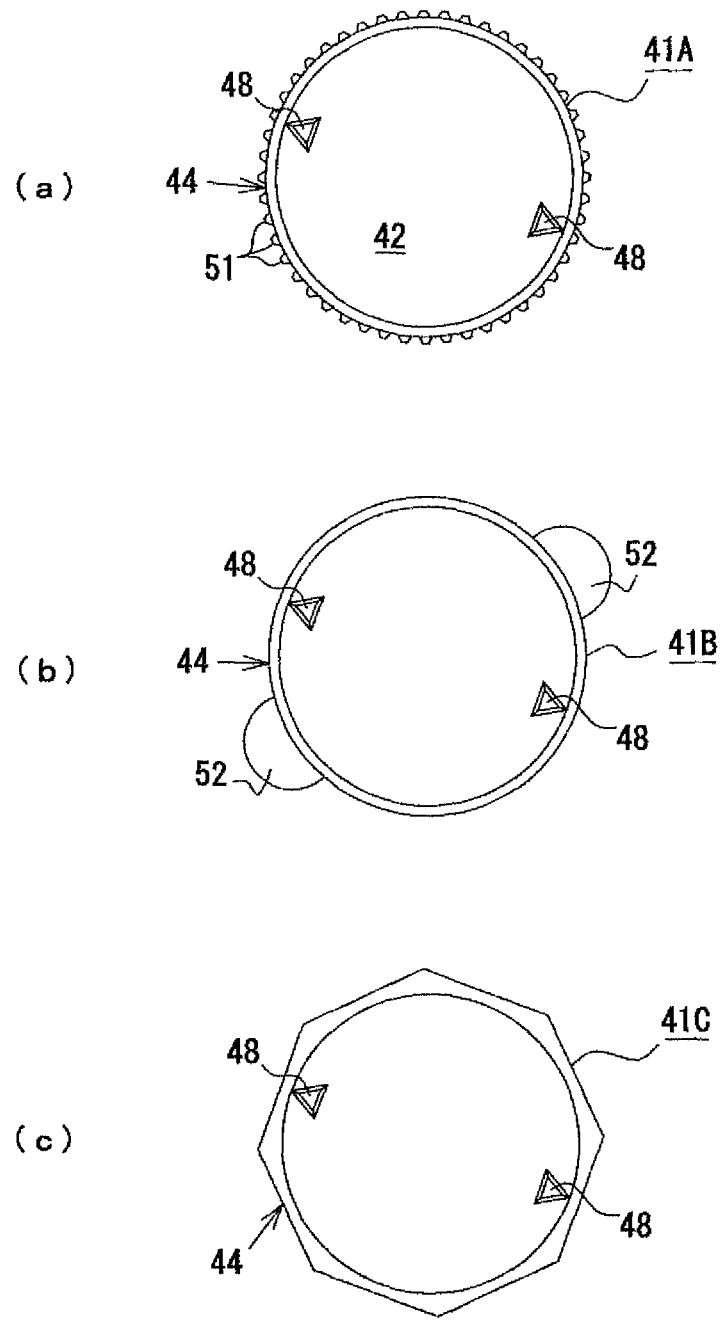
FIG. 5(a) to (c) are plan views showing separate embodiments of the securing member of the presently disclosed catheter fixing tool.

Cover 41 as the securing member may be configured, for example, as follows. In cover 41A of a separate embodiment shown in FIG. 5(*a*), a plurality of nonslip salient parts 51 are provided for on the circumferential surface of cover 41A. In cover 41B of a separate embodiment shown in FIG. 5(*b*), opposing semicircular-shaped finger holds are provided in two locations on the circumferential surface of cover 41B. In cover 41C of a separate embodiment as shown in FIG. 5(*c*), the cover has a shape that appears as a polygon in a plan view (a hexagon here). According to these configurations, when a practitioner turns covers 41A to 41C, it becomes easier for the fingers to grab the circumferential part 44 of cover 41, and rotational manipulation can be done easily.

Figure 6:
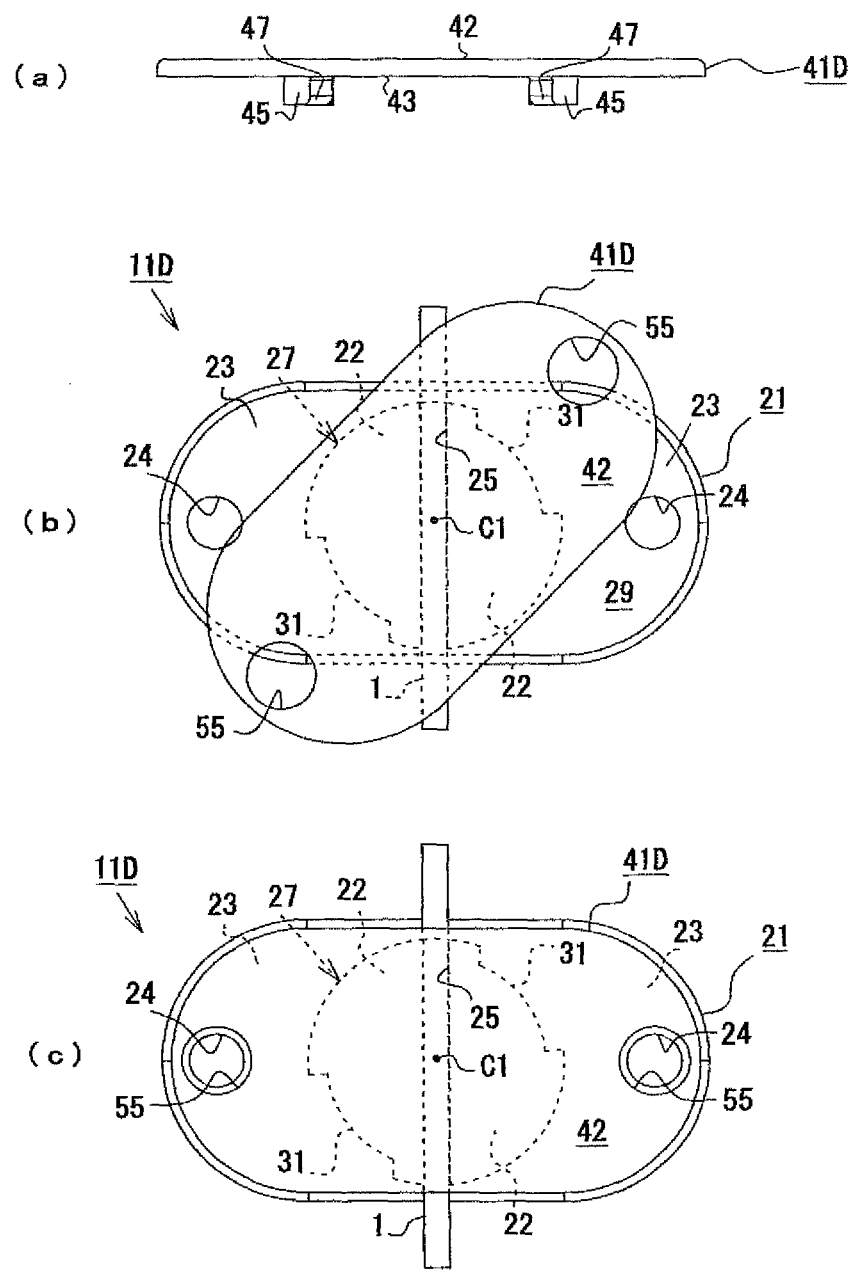
FIG. 6(a) is a front view showing separate embodiments of the securing member of the presently disclosed catheter fixing tool; (b) is a plan view before the securing member is rotationally interlocked with the fixing tool main body; and (c) is a plan view showing after the securing member is rotationally interlocked with the fixing tool main body.

In the aforementioned embodiments, the size of securing member covers 41 and 41A to 41C is about half the size of fixing tool main body 21, and while positioned so as to be in the center part of fixing tool main body 21, it is not limited to this location. For example, a configuration such as cover 41D of catheter fixing tool 11D of a separate embodiment shown in FIG. 6 may be adopted. This cover 41D presents an oblong shape similar to fixing tool main body 21, and is formed slightly smaller than fixing tool main body 21. In addition, through holes 55 are provided at both ends of cover 41, respectively. These through holes 55 correspond to the locations of holes 24 in fixing tool main body 21 and are formed with a slightly smaller diameter than holes 24.

In the aforementioned embodiments, cover 41 was considered to be composed of an opaque resin material, but it may be composed of a transparent resin material.

In the aforementioned embodiments, the triangular positioning marks 48 and the arrow-shaped positioning marks were made in combination so as to understand the positioning status, but positional marks including of graphic forms different than this may be adopted. In addition, positioning marks may be omitted when not particularly necessary. That is, in the catheter fixing tool 11D shown in FIG. 6, positioning marks have been omitted, but the positioning status can be understood by the location of through holes 55 relative to holes 24.

Next, the technical ideas understood by the embodiments described above are enumerated below.

(1) In paragraph 1 of any of aforementioned embodiments 1 to 4, the aforementioned fixing tool main body and the aforementioned securing member can be both made of resin.

(2) In paragraph 1 of any of aforementioned embodiments 1 to 4, the aforementioned securing member can include an opaque resin material.

(3) In paragraph 1 of any of aforementioned embodiments 1 to 4, the locking recessed part formed in the aforementioned guided part of the aforementioned securing member can include a protrusion that can be engaged in the aforementioned retaining part when the aforementioned securing member is fully interlocked.

(4) In paragraph 1 of any of aforementioned embodiments 1 to 4, the aforementioned securing member can include a harder material than the aforementioned fixing tool main body.

(5) In paragraph 1 of any of aforementioned embodiments 1 to 4, positioning marks can be provided, respectively, in the aforementioned fixing tool main body and the aforementioned securing member.

(6) In paragraph 1 of any of aforementioned embodiments 1 to 4, the aforementioned securing member need not protrude out from the aforementioned fixing tool main body during the aforementioned rotational interlocking motion and when rotational interlocking is complete.

(7) In paragraph 1 of any of aforementioned embodiments 1 to 4, the aforementioned securing member can be a circular plate-shaped member.

(8) In paragraph 1 of any of aforementioned embodiments 1 to 4, the aforementioned securing member need not cover the holes provided in the aforementioned wing parts when interlocking motion is complete.

(9) In paragraph 1 of any of aforementioned embodiments 1 to 4, the aforementioned securing member can be composed of a different form than the aforementioned fixing tool main body.

(10) In paragraph 1 of any of aforementioned embodiments 1 to 4, the aforementioned fixing tool main body can be fixed to the skin.

What is claimed is:

1. A catheter fixing tool for securing a tubular catheter to a patient comprising a plate-shaped fixing tool main body having a retaining part, into which is formed a catheter retaining slot, and pair of wing parts, and a securing member that can be interlocked with the fixing tool main body by rotation of the securing member parallel to a principal plane of the fixing tool main body taking a virtual line perpendicular to the principal plane of the fixing tool as a central axis, wherein the retaining part is pressed by the securing member to constrict the catheter retaining slot when rotationally interlocked with the securing member.

2. The catheter fixing tool described in claim 1, wherein the securing member is shaped to be smaller than the fixing tool main body in a plan view, and the virtual line is set roughly in a center of the retaining part and roughly in a center of the securing member in a plan view.

3. The catheter fixing tool described in claim 1, wherein the securing member is a cover that completely covers the retaining part in a state where a back side of the securing member is brought into contact with a top of the retaining part.

4. The catheter fixing tool described in claim 1, wherein guide parts extending in a principal surface direction of the fixing tool main body are provided in an outer peripheral surface of the retaining part, and guided parts configured to lock into the guide parts are provided in an external peripheral part of a back side of the securing member.

* * * * *